United States Patent [19]
Välilä

[11] 4,241,254
[45] * Dec. 23, 1980

[54] X-RAY SOURCE MOVING MECHANISM SUITABLE FOR PANORAMIC RADIOGRAPHY

[75] Inventor: Veikko F. Välilä, Vantaa, Finland

[73] Assignee: Syntex (U.S.A.) Inc., Palo Alto, Calif.

[*] Notice: The portion of the term of this patent subsequent to Mar. 20, 1996, has been disclaimed.

[21] Appl. No.: 963,463

[22] Filed: Nov. 24, 1978

Related U.S. Application Data

[63] Continuation of Ser. No. 858,431, Dec. 7, 1977, Pat. No. 4,145,611.

[30] Foreign Application Priority Data

Dec. 10, 1976 [FI] Finland .................................. 763569

[51] Int. Cl.³ .............................................. G03B 41/16
[52] U.S. Cl. ................................................. 250/439 P
[58] Field of Search ............... 250/439 R, 439 P, 523, 250/490

[56] References Cited

U.S. PATENT DOCUMENTS 3,536,913  10/1970  Huchel ............................. 250/439 P
4,039,837  8/1977  Ohta ................................. 250/439 P

*Primary Examiner*—Craig E. Church
*Attorney, Agent, or Firm*—Joseph I. Hirsch; John A. Dhuey

[57] ABSTRACT

A mechanism for moving an X-ray source around the patient's head so that the image of an object, having shape of the dental arch, can be obtained on the film, the mechanism including a stationary frame, a rotatably movable support arm with an X-ray source and a film holder attached to its opposite ends on different sides of the object to be radiographed, and means for moving the center of rotation of the support arm rectilinearly during the radiographing, throughout the procedure in the same direction, perpendicular to the axis of symmetry of the dental arch, in such a manner that the position of the center of rotation in its rectilinear movement is dependent on the angular position of the support arm at any given moment, with the purpose of directing the X-ray beam from the X-ray source so that at any given moment it is substantially perpendicular to that part of the object which has the shape of the dental arch.

12 Claims, 3 Drawing Figures

X-RAY SOURCE MOVING MECHANISM SUITABLE FOR PANORAMIC RADIOGRAPHY

This is a continuation, of application Ser. No. 858,431, now U.S. Pat. No. 4,145,611 filed Dec. 7, 1977.

BACKGROUND OF THE INVENTION

1. Field of the Invention

The present invention relates to a mechanism for moving an X-ray source in order to obtain, on an X-ray film, panoramic radiographs of an object the shape of the dental arch. The mechanism is of the type which comprises a stationary frame, a movable support arm with the source of radiation and the film holder attached at its opposite ends on both sides of the object to be radiographed, and means for effecting the rotational movement of the support arm around the object.

2. Description of the Prior Art

In panoramatomographic radiography technique, an image of a layer of the object, the layer being of a certain depth, is formed on the film. The shape, location and thickness of this image layer can be affected by a suitable arrangement of the geometry relating to the forming of an image of the object. Normally in this technique, the X-ray source and the film move in relation to the patient, who is therefore immobile during the radiographing. A precise image of the desired spot of the object is formed on the film, if the velocity of the film is selected equal to the velocity of the projected image of the spot being radiographed on the film surface.

The following factors, among others, affect the results obtained in panoramatomographic radiography: the distance of the center of rotation of the X-ray source from the object being radiographed, the film and the X-ray source, the velocity of the film in relation to the velocities of the image spots of the object projected onto the film surface, the width of the X-ray beam on the film surface, the size of the focal spot of the X-ray source, the type of X-ray film used, the properties of the intensifying screens, and the quality and amount of radiation emitted by the source. The significance of these factors is explained in more detail in, for example, J. van Aken's article: Panoramic X-ray equipment, Reports of Councils and Bureaus/Joda, Vol. 86, May 1973. The most important equipment available on the market and the principles of operation of the same are also described in the said publication.

There are currently available several panoramic X-ray apparatus, developed by different manufacturers. One of the basic models is the Finnish Orthopantomograph, developed by T. Nieminen on the basis of Professor Y. Paatero's idea and manufactured by Palomex Oy. In the said apparatus, the patient is in a standing position during the radiographing; the X-ray source and the film holder move around the patient's head while the patient remains immobile. In the apparatus, the rotational movement of the X-ray source has three different fixed rotation centers; change from one rotation center to another is through a cycloidal movement.

In the apparatus marketed by S. S. White (U.S. Pat. No. 3,045,118), the patient is in a sitting position, the X-ray source has during the radiographing two different rotation centers in relation to the patient, but the X-ray source rotates around the same point throughout the procedure, in which case the change from one rotation center to another takes place by shifting the patient laterally over a suitable distance with the aid of the chair. This system has a disadvantage in that radiographing is not possible during the shifting, in which case the central area in the X-ray film must be left unexposed and thus the front teeth, which are in the middle of the dental arch, are not radiographed. In GE-3000 manufactured by General Electric (German (FRG) Patent Application No. 1 955 294), the movement of the rotation center of the source of X-ray radiation is based on a pair of elliptic gears and takes place along a curved path in a manner determined by the dimensioning of the gear pair.

Japanese Panex-"E" of Morita Corporation is a kind of application of the ellipsograph. Its principle of operation is disclosed in German (FRG) Patent Applications Nos. 2 057 135, 2 252 578 and 2 252 579. In this apparatus also, the rotation center of the X-ray source moves along a curved path.

There are also other similar apparatus on the market, but the mechanisms moving the X-ray source in these systems do not deviate substantially from the basic types mentioned above.

The point of departure in planning the mechanisms of all the apparatus currently on the market is some geometric curve close to the shape of the jaw bone, either an ellipse or a combination of two or three arcs of a circle, since thereby rather simple mechanisms can be constructed for moving the source of radiation.

However, if the planning is based on a shape as close to the jaw bone shape as possible and the optimal movement of the rotation center of the X-ray source in that case is determined thereafter, it is observed that the shape does not follow precisely any definite simple geometric shape. From this it follows that the movement used in current radiographic equipment is always to a certain extent an inaccurate approximation of the ideal.

SUMMARY OF THE INVENTION

The present invention provides a mechanism of the character once described, which comprises a stationary frame, a rotatable support arm, an X-ray source attached to one end of the support arm, a film holder attached to the opposite end of the support arm, means for positioning the patient's head in the space between the X-ray source and the film holder, and means for moving the center of rotation of the support arm, during the radiographing, rectilinearly in a direction perpendicular to the axis of symmetry of the dental arch, in such manner that the position of the center of rotation is dependent, in its rectilinear movement, on the angular position of the support arm at any given moment, with the purpose of directing the X-ray beam from the X-ray source so that at any given moment it is substantially perpendicular to that part of the object having the shape of the dental arch.

The object of the present invention is to eliminate the disadvantages of known equipment and to provide a panoramic X-ray apparatus for radiographing especially an object the shape of the dental arch, an apparatus in which the movement of the X-ray source has been implemented in an ideal manner, corresponding to a general jaw bone shape. The essential idea in the invention is that, when the movement of the X-ray source is divided into linear and rotational components is prior known and the desired movement is effected as a synchronization of these two partial components, the linear component of the movement is perpendicular to the axis of symmetry of the dental arch.

When the movement of the X-ray source is divided into rotational and linear components, there are primarily two alternatives: the linear component is parallel to the axis of symmetry of the dental arch, or it is perpendicular to it. An apparatus according to the first alternative, however, involves certain technical problems. If the rectilinear movement takes place parallel to the axis of symmetry of the dental arch, the movement changes its direction at the half-way point of the radiographing, which may be technically difficult to control in terms of an even, disturbance-free progress of the movement involved in the radiographing. Another problematic factor consists of the fact that the acceleration of the linear movement is at its greatest at the beginning and at the end of the movement; this is also difficult to control so as to eliminate undesirable jerks at the beginning of the movement.

However, if the linear movement of the source of radiation takes place perpendicular to the axis of symmetry of the dental arch according to the present invention, the above drawbacks do not exist, the direction of the linear movement remains unchanged throughout the procedure; and in addition, the velocity of the movement slowly begins to increase at the beginning of the procedure, at its middle the velocity of the linear movement is at its maximum, whereafter the velocity again decreases evenly until it reaches zero. Such an evenly increasing and decreasing movement is easier to control; the evenness of and the lack of vibration in the movement involved in panoramic X-ray photography is of primary importance in terms of successful radiography.

DESCRIPTION OF THE PREFERRED EMBODIMENT

Figure 1:
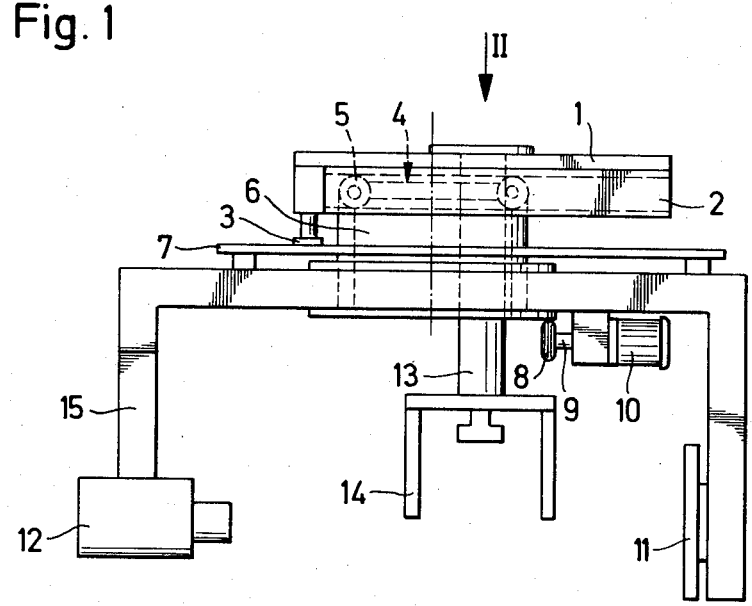
FIG. 1 depicts schematically a side view of one embodiment of the moving mechanism according to the invention.
Figure 2:
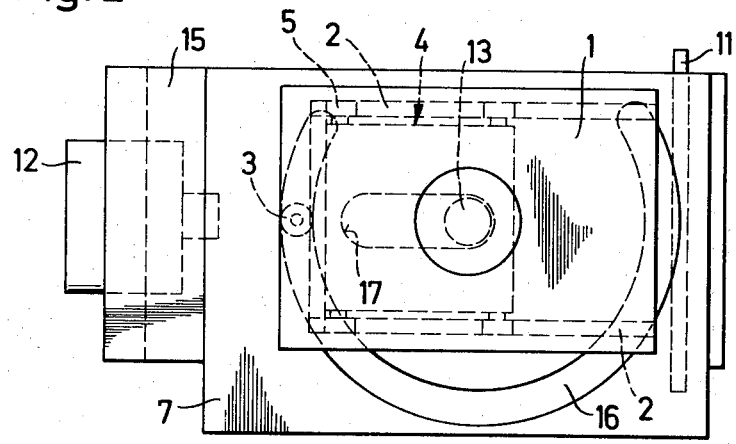
FIG. 2 depicts a plan view of the mechanism according to FIG. 1.

In the moving mechanism depicted in the figures, some parts, especially those which belong to the frame, have been left undepicted for the sake of clarity.

A plate 1 has been attached to the frame of the apparatus through frame members not depicted. On both sides of the plate 1 there are members 2 which have running grooves for the bearings 5. The plate 1 and the members 2 constitute the stationary frame of the moving mechanism. Also attached to the frame is a guide pin 3, which moves in the groove 16 in the grooved plate 7.

Moving rectilinearly in relation to the frame, there is a plate 4; the bearings 5 moving in the running grooves in the members 2 have been attached to the plate 4. Attached to the plate 4, there is a member 6 to which a support arm 15 has been pivoted. The center point of the bearing of the member 6 is the rotation center of the pivoting movement of the support arm 15. In the member 6 there is an opening 17 through which the attachment member 13 has been attached to the plate 1. Head positioners 14 have been suspended from the attachment member 13. The plate 4, the bearings 5, and the member 6 constitute the rectilinearly moving member of the movement mechanism, i.e. the linear section.

The X-ray source 12 and the film holder 11 have been suspended from the support arm 15, and a rotatable axle 9 with a drive wheel 8 has been attached to it. The axle 9 is rotated by an electric motor 10. The drive wheel 8 moves, rotated by the electric motor 10, along the surface of the member 6, owing to friction between the drive wheel 8 and the member 6, whereby the support arm 15 pivots relative to the member 6, supported by the bearings between the member 6 and the support arm 15. The grooved plate 7 with a groove 16 has been attached to the support arm 15. When the support arm 15 pivots, the guide pin 3 moves along the groove 16. Since the distance of the groove 16 from the member 6, i.e. from the center of rotation of the support arm 15, is variable and the guide pin 3 has been attached to the plate 1 of the frame, the plate 4 and the member 6 attached to it move rectilinearly relative to the frame while the support arm 15 pivots relative to the member 6.

Figure 3:
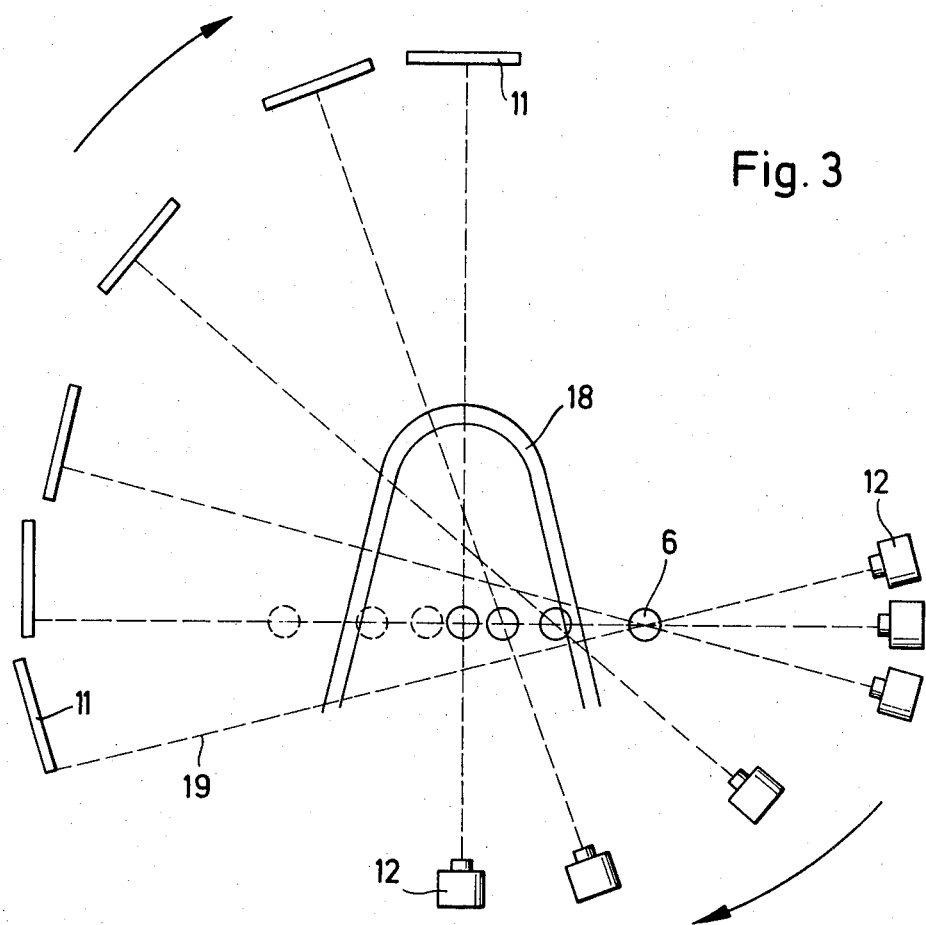
FIG. 3 depicts the principle of operation of the mechanism moving the X-ray source in relation to the dental arch.

The patient's head (not shown) is situated between the X-ray source 12 and the film holder 11, supported by the head positioners 14 shown in FIG. 1. The dental arch 18 in the patient's head is situated in the manner shown in FIG. 3 relative to the moving mechanism. FIG. 3 also shows the movement of the X-ray beam 19 relative to the dental arch.

The X-ray source 12 is on the right at the beginning of the radiographing, from where it moves, as shown in figure, to the middle, at which time the procedure is half-way completed. At the middle, the X-ray source 12 continues in the same direction to the left so that the radiographing movement is a continuous, even movement, symmetric in relation to the axis of symmetry of the dental arch.

The inventional idea in the mechanism described above is as follows. It was required of the mechanism to be implemented that the X-ray source 12 should move, relative to the dental arch 18, in the optimal manner in terms of the projection of the teeth. It was also required that the mechanism could be implemented in such a manner that mechanical movements during the radiographing should be as continuous and vibration-free as possible so as to eliminate defects due to vibration in the radiograph. The bearings of the mechanism were to be simple in order to achieve the necessary steadiness. The simplicity of the mechanism makes low-cost production possible, which also makes the invention commercially significant.

The invention is characterized by the fundamental observation that the movement of the center of rotation of the X-ray source 12 can be effected using a unidirectional movement. In such a case the movement of the X-ray source 12 is a combination of a continuous rotational movement and a unidirectional rectilinear movement. The unidirectional movement has been implemented according to the principle of a cam, by means of a guide pin 3 and a grooved plate 7; the distance of the groove 16 in the grooved plate 7 from the center of rotation, i.e. the member 6, has been chosen so as to ensure that the X-ray source 12 radiographs a layer 18 of the correct anatomical shape and thickness in such a manner that the X-ray beam 19 is as perpendicular as possible to the layer 18 being radiographed. Such a perpendicular projection, in which the dimensions of the image are correct, is diagnostically much more informative and easier to read.

It is evident that the moving mechanism of the described type is easy to implement in practice since in it the moving mass has been attached simply by using one rotational and one linear bearing. A model of the moving mechanism was made, and using this model it was observed that the mechanism fulfilled the requirements set on it.

In the moving mechanism according to the invention, the movement of the support arm 15 can be effected by means of transmission provided between the member 6 and the support arm 15; in practice, the friction drive illustrated in FIG. 1 seems to be an alternative which is superior to, for example, belt, chain or gear transmission, which may cause vibration in the movement of the support arm 15.

The moving mechanism according to the invention can also be used with a patient in a lying position, in which case the linear section moves advantageously in a horizontal plane and the electric motor 10 driving the X-ray source 12 need not be very powerful.

It is evident that the embodiments described can be varied without deviating from the idea of the invention. However, an inexpensive, very sturdy but still precise moving mechanism can be implemented in the manner described above.

What is claimed is:

1. A mechanism for moving an X-ray source and an X-ray sensitive film holder around a patient's head so that the image of an object, having at least partially the shape of a dental arch, can be obtained on the film; said mechanism comprising:
    a stationary frame,
    a rotatable support arm having a center of rotation,
    an X-ray source attached to one end of the support arm,
    a film holder attached to the opposite end of the support arm,
    means for positioning the patient's head between the X-ray source and the film holder, and
    means for moving the center of rotation of the rotatable support arm, during the radiographic procedure, along a rectilinear path perpendicular to the axis of symmetry of the dental arch, in such manner that the position of the center of rotation along the rectilinear path is dependent at any given moment on the angular position of the support arm so that the X-ray beam from the X-ray source at any given moment during the radiographic procedure is directed substantially perpendicular to that part of the object having the shape of the dental arch.

2. The moving mechanism according to claim 1 wherein the stationary frame is provided with a rectilinearly movable member, the support arm being pivoted to the rectilinearly movable member and moving the rectilinearly movable member relative to the stationary frame during rotation thereof.

3. The moving mechanism according to claim 2 further including a rotatable axle attached to the support arm, and transmission means between the axle and the rectilinearly movable member for effecting the rotational movement of the support arm relative to the rectilinearly movable member.

4. The moving mechanism according to claim 2 wherein the support arm is operatively connected to a plate having a groove therein, the frame has a guide pin which follows, when the support arm rotates, the groove in the plate, such that during the radiographic procedure the center of rotation of the support arm moves in relation to the stationary frame in the manner determined by the shape of the groove.

5. The moving mechanism according to claim 2 wherein the support arm is operatively connected to the rectilinearly movable member by means of a bearing, said mechanism further including an attachment member connected to the frame, and head positioning means suspended from the attachment member, the attachment member extending from the stationary frame through the middle of the bearing and through an opening in the rectilinearly movable member.

6. The moving mechanism according to claim 3 wherein the movement of the rotatable axle is effected by an electric motor connected to the axle and supported by the support arm.

7. The moving mechanism according to claim 3 wherein the movement of the rotatable axle is transmitted to the rectilinearly movable member by means of friction drive between a drive wheel on the axle and a member operatively connected to the rectilinearly movable member.

8. The moving mechanism according to claim 2 further including means for effecting the rotational movement of the support arm relative to the rectilinearly movable member.

9. A mechanism for moving an X-ray source and an X-ray sensitive film holder around a patient's head so that the image of an object, having at least partially the shape of a dental arch, can be obtained on the film; said mechanism comprising:
    a stationary frame,
    a rectilinearly movable member supported by said stationary frame,
    a rotatable support arm supported by said rectilinearly moveable member, said rotatable support arm having a center of rotation,
    said rotatable support arm being pivotally mounted with respect to said rectilinearly movable member so as to move said rectilinearly movable member relative to said stationary frame during rotation of said rotatable support arm,
    an X-ray source attached to one end of said support arm,
    a film holder attached to the opposite end of said support arm,
    means for positioning the patient's head between said X-ray source and said film holder, and
    means for effecting the rotational movement of said rotatable support arm relative to said rectilinearly movable member such that the center of rotation of said rotatable support arm, during the radiographic procedure, is moved along a rectilinear path perpendicular to the axis of symmetry of the dental arch, in such manner that the position of the center of rotation along the rectilinear path is dependent at any given moment on the angular position of said rotatable support arm so that the X-ray beam from said X-ray source at any given moment during the radiographic procedure is directed substantially perpendicular to that part of the object having the shape of the dental arch.

10. The moving mechanism according to claim 9 wherein said support arm is operatively connected to a plate having a groove therein, said stationary frame has a guide pin which follows, when said support arm rotates, said groove in said plate such that, during the radiographic procedure, the center of rotation of said support arm moves in relation to said stationary frame in the manner determined by the shape of said groove.

11. A mechanism for moving an X-ray source and an X-ray sensitive film-containing holder around a patient's head so that the image of an object, having at least partially the shape of a dental arch, can be obtained on the film;

said mechanism comprising:
a stationary frame,
a rectilinearly movable member supported by said stationary frame,
a rotatable support arm supported by said rectilinearly moveable member, said rotatable support arm having a center of rotation,
said rotatable support arm being pivotally mounted with respect to said rectilinearly movable member,
said rotatable support arm and said rectilinearly movable member moving relative to each other during rotation of said rotatable support arm and rectilinear movement of said rectilinearly movable member,
an X-ray source attached to one end of said rotatable support arm,
a film holder attached to the opposite end of said rotatable support arm,
means for positioning the patient's head between said X-ray source and said film holder, and
means for effecting the rotational movement of said rotatable support arm relative to said rectilinearly movable member such that the center of rotation of said rotatable support arm, during the radiographic procedure, is moved along a rectilinear path perpendicular to the axis of symmetry of the dental arch, in such manner that the position of the center of rotation along the rectilinear path is dependent at any given moment on the angular position of said rotatable support arm so that X-ray beam from said X-ray source at any given moment during the radiographic procedure is directed substantially perpendicular to that part of the object having the shape of the dental arch.

12. The moving mechanism according to claim 11 wherein said rotatable support arm is operatively connected to a plate having a groove therein, said stationary frame has a guide pin which follows, when said rotatable support arm rotates, said groove in said plate, such that, during the radiographic procedure, the center of rotation of said rotatable support arm moves in relation to said stationary frame in the manner determined by the shape of said groove.

* * * * *